United States Patent [19]

Martinez et al.

[11] Patent Number: 4,781,693
[45] Date of Patent: Nov. 1, 1988

[54] INSULIN DISPENSER FOR PERITONEAL CAVITY

[75] Inventors: Felix J. Martinez, Plymouth; Larry E. Fuller, Minnetonka; Louis C. Cosentino, Wayzata, all of Minn.

[73] Assignee: Minntech Corporation, Minneapolis, Minn.

[21] Appl. No.: 529,048

[22] Filed: Sep. 2, 1983

[51] Int. Cl.$^4$ ............................................. A61F 1/00
[52] U.S. Cl. .................................... 604/175; 604/244
[58] Field of Search ................... 604/29, 49, 53, 175, 604/244, 256, 283, 415, 905, 86; 128/1 R

[56] References Cited

U.S. PATENT DOCUMENTS

| | | | |
|---|---|---|---|
| 4,133,441 | 1/1979 | Mittleman et al. | 604/86 |
| 4,306,976 | 12/1981 | Bazzato | 604/29 |
| 4,405,320 | 9/1983 | Cracauer et al. | 604/175 |
| 4,488,877 | 12/1984 | Klein et al. | 604/244 |
| 4,512,761 | 4/1985 | Raible | 604/175 |

OTHER PUBLICATIONS

"The Peritoneum-A Potential Insuline Delivery Route for a Mechanical Pancreas", by David S. Schade and Philip Eaton, reprinted from Diabetes Care, vol. 3, No. 2, Mar.-Apr., 1980.
"Stabilization and Improvement of Renal Function in Diabetic Nephrophathy", by Robert L. Stephen et al, published in Diabetic Nephropathy, vol. 1, No. 1, 11/82.
"Multiple Daily Insulin Injections Through Subcutaneously Implanted Needle, by G. Slama et al, printed in Letters to the Editor in The Lancet, 5/1980, p. 1780.
"The Role of Biomaterials in Insulin Delivery Systems", by S. D. Brucke, The international Journal of Artificial Organs, vol. 3, No. 5, 1980, pp. 299-304.
"A Review of Programmed Insulin Delivery Systems", by W. J. Spencer, IEEE Transactions on Biomedical Engineering, vol. ME-28, No. 3, Mar. 1981.
"Multiple Use of Disposable Insulin Syringe-Needle Units", by Robert Hodge, Jr. et al, JAMA, 7/18/80, vol. 244, No. 3.
"Outpatient Treatment of Juvenile-Onset Diabetes with a Preprogrammed Portable Subcutaneous Insulin Infusion System", by W. V. Tamborlane, et al, The American Journal of Medicine, vol. 68, 2/1980.
"Intraperitoneal Administration of Insulin During Peritoneal Dialysis of Diabetics with Terminal Renal Failure", by K. E. Hemmeloff Andersen et al, The International Journal of Artificial Organs, vol. 4, No. 4, 1981, pp. 162-167.
"Continuous Ambulatory Peritoneal Dialysis in Diabetic Patients", by C. T. Flynn Capd in Diabetes, pp. 187-193.
"The Peritoneal Absorption of Insulin in Diabetic Man: A Potential Site for a Mechanical Insuline Delivery System", by D. S. Schade, et al, Metaorganism, vol. 28, No. 3, Mar. 1979.
"Investigations of Risks and Hazards with Devices Associated with Peritoneal Dialysis (Including Intermittent Peritoneal Dialysis and Continuous Ambulatory Peritoneal Dialysis) and Sorbent Regenerated Dialysate Delivery Systems, revised Draft Report for FDA Contract No. 223-81-5001 (6/82).

Primary Examiner—John D. Yasko
Attorney, Agent, or Firm—Vidas & Arrett

[57] ABSTRACT

An implant device for introduction of insulin into the peritoneal cavity which permits a flexible catheter to be removed and replaced without invasive surgery. The catheter is passed through a substantially rigid percutaneous body and a distally extending catheter conduit which together form a continuous conduit from the body exterior through the peritoneal wall. A polytetrafluoroethylene polymer sleeve allows tissue ingrowth to secure the body to the epidermis. A polyethylene terephthalate portion of the sleeve provides tissue ingrowth to stabilize the implant and prevent extrusion from the dermis. The catheter is associated with the percutaneous tubular body so as to be removable and replaceable through the conduit thereformed after implantation. The catheter preferably terminates within the interior cavity of the percutaneous body and is sealed from the environment by means of a septum closure within the device cavity. A sponge saturated with antiseptic is fitted in the body recess above the septum and is closed off from the environment by a penetrable cap member. The saturated sponge prevents the introduction of bacteria into the peritoneum.

2 Claims, 2 Drawing Sheets

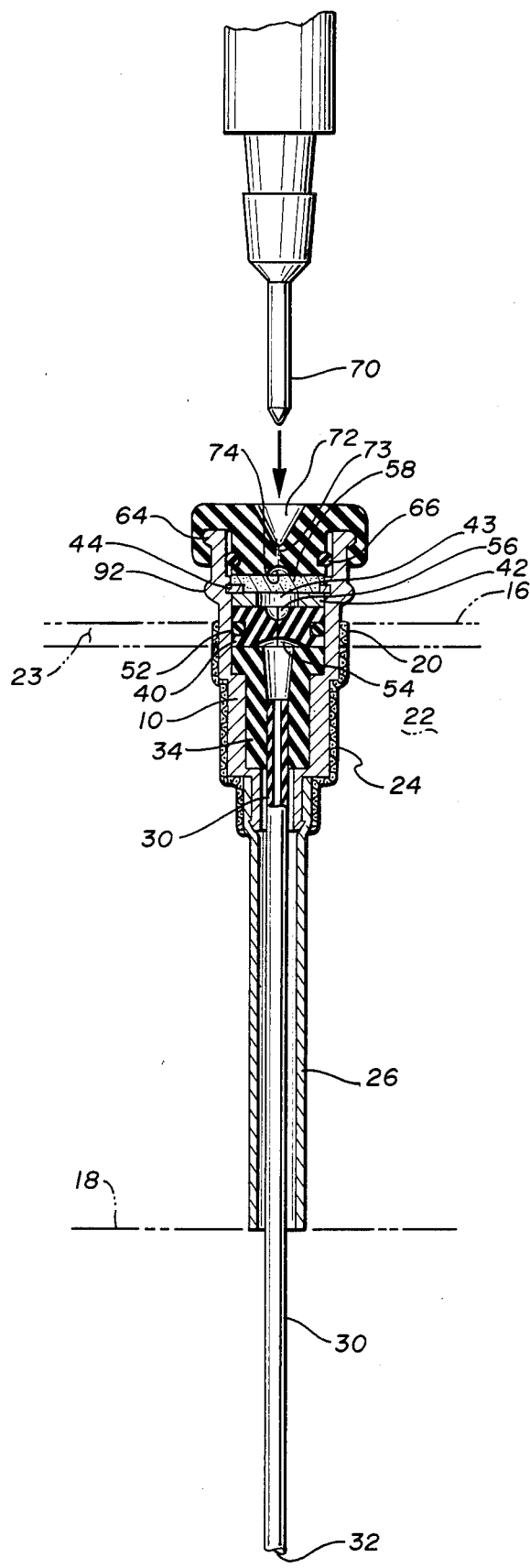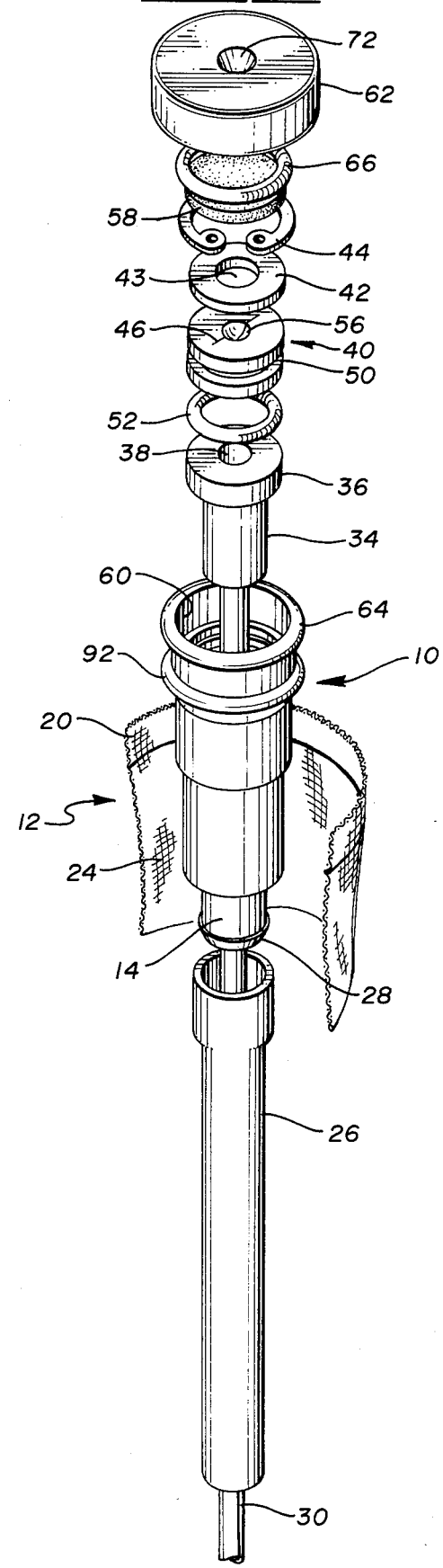

INSULIN DISPENSER FOR PERITONEAL CAVITY

BACKGROUND OF THE INVENTION

1. Field of the Invention

This invention relates to the field of implantable percutaneous devices and more particularly to the field of devices used in dispensing insulin into the peritoneal cavity.

2. Description of the Prior Art

Diabetes mellitus is a chronic systemic disease afflicting about 10 million Americans. Diabetes is currently the third leading cause of death in the United States and is the principal cause of blindness among adults. It is believed that improved blood glucose control will reduce the longterm complications of diabetes. Currently, diabetes is controlled daily by single or multiple subcutaneous injections of combinations of regular and long-acting insulins. Subcutaneous injections tend to prevent severe hyperglycemia and offering advantages over intramuscular injection of insulin thereby permitting the insulin-dependent diabetic to survive.

Since a normal pancreas secretes all its insulin into the portal vein, delivery of insulin into this site would be more "physiologic." The peritoneum has been suggested as an insulin delivery site.

Intro-peritoneal delivery of insulin allows insulinization of the liver without peripheral hyperinsulinemia, rapid and predictable insulin absorption and eliminates blood clotting at the tip of the delivery catheter. Injection of insulin through a peritoneal implant mimics the physiologic route of insulin released by the pancreas and avoids the disadvantages inherent in intramuscular delivery of insulin.

A second contemplated use for the device of the invention is in connection with peritoneal dialysis. Peritoneal dialysis has been accomplished to date by means of a flexible catheter which is implemented so as to pass directly through the skin and peritoneal wall into the peritoneal cavity. A recent detailed review of devices associated with peritoneal dialysis may be found in Ward et al, "Investigation of the Risks and Hazards with Devices Associated with Peritoneal Dialysis (Including Intermittent Peritoneal Dialysis and Continuous Ambulatory Peritoneal Dialysis) and Sorbent Regenerated Dialysate Delivery Systems," revised draft report for FDA contract No. 223-81-5001 (June, 1982).

Despite extensive protocols for maintaining sterility, infection frequently occurs as a result of peritoneal dialysis. The most common infection pathway is through the interior of the catheter but exit site infection caused by bacteria invasion along the exterior surfaces of the catheter occurs as well.

Improvements in prior art peritoneal dialysis implants are described in co-pending applications Ser. No. 314,569, filed Oct. 26, 1981; Ser. No. 410,365, filed August 23, 1982, and U.S. Pat. No. 4,417,888 all of which have a common assignee with the present application. The improvements of these prior applications comprise rigid tubular percutaneous devices implanted through the skin to which a catheter member is affixed subcutaneously. Access to the peritoneum in these devices is accomplished through a sterile needle assembly which enters a septum.

Co-pending applications Ser. Nos. 314,569; 410,365 and U.S. Pat. 4,417,888 are incorporated herein by reference to illustrate the state of the art in peritoneal dialysis implants.

Robert L. Stephen identifies an intra-peritoneal insulin access device in "Stabilization and Improvement of Renal Function in Diabetic Nephropathy" in 1 Diabetic Nephropathy 8 (November, 1982). The device shown therein consists of a polyurethane bowl and stem which is completely embedded within and under the skin such that an epidermal layer covers the entire surface. Such a device still requires the passage of a needle through body tissue to enter the device.

BRIEF SUMMARY OF THE INVENTION

The present invention provides an implantable device for dispensing insulin or other chemical agents into the peritoneal cavity. A substantially rigid tubular body of biologically compatible material extends through the skin after implantation so as to provide a fluid passageway for accessing the peritoneal cavity through the interior of the tubular body. A flexible sleeve member surrounds the tubular percutaneous body. The sleeve length is sufficient to pass through the tissue between the tubular body and the peritoneal wall. The flexible sleeve member is formed of a biologically compatible material which has sufficient porosity to permit tissue ingrowth therein and has insufficient porosity to permit substantial leakage of peritoneal fluids into the tissue surrounding the sleeve. In the preferred form, the sleeve member which contacts the epidermis is formed of an expanded polytetrafluoroethylene polymer and the remainder of the sleeve member is formed of a porous polyethylene terephthalate polymer. It is believed that the use of a polytetrafluoroethylene polymer provides better tissue ingrowth in the outer-most, nonvascular epithelial layer of skin.

A tubular biologically compatible conduit extends downwardly from the tubular body such that is passes into the peritoneal cavity. The conduit provides a guide for a flexible catheter member. The flexible catheter member is inserted through the tubular body from the skin side and is guided through the conduit where its free end may be positioned by a physician. The catheters are held in place to the tubular body by means of a flared end. An elastomeric septum is positioned in sealing relationship in the tubular body and is compressed between a support extension within the tubular body and a pressure plate above the septum. The septum is provided with preformed openings therethrough to provide a releasable pathway for a needle.

A locking ring holds the septum member and flexible catheter within the tubular body. An excutaneous cavity is defined above the septum within the tubular body. A sponge saturated with an antiseptic solution is placed within the excutaneous cavity to provide a sterile barrier.

The percutaneous implant includes a penetrable cap member which seals the sponge within the tubular body. The cap member preferably includes a cone-shaped depression as a guide for the cannula or needle. The cap member preferably includes an integral O-ring which creates a seal when the cap member is snapped over the tubular body.

Syringes, pumps or other solution dispensing systems are connected to the cannula. The cannula is preferably formed with a round bore at its tip which passes through the penetrable cap member, sponge and septum. Fluid can therefore be injected through the catheter directly into the peritoneal cavity.

The peritoneala access device of the invention provides an implant which becomes securely anchored to the body by tissue ingrowth into the porous material without the need for a subcutaneous stabilizing flange. The use of a polytetrafluoroethylene sleeve through the epidermis and a polyethylene terephthalate sleeve through the dermis or vascular layer of skin tissue provides excellent attachment of the device to the skin. The construction allows a nonsurgical, uncomplicated removal of the catheter should cloggage mandate replacement of the catheter.

In operation, the saturated sponge provides a bacterial barrier through its bactericidal or bacteriostatic action. Bacterial introduction through hollow needles or cannulas is lessened due to the saturated sponge barrier. Chemicals within the sponge tend to destroy any bacteria which may be introduced by the needle or cannula thereby lessening the chance of peritonitis.

The catheter is easily removed from the body due to the catheter conduit design which lessens the chance of tissue ingrowth to the catheter itself. The catheter can be removed while the tubular body remains firmly secured to the skin.

BRIEF DESCRIPTION OF THE DRAWINGS

The detailed description of the invention, including its preferred embodiment, is hereinafter described with specific reference being made to the drawings in which:

FIG. 1 is a cross sectional view of the device of the invention showing skin lines and a cannula of the invention.

FIG. 2 is an exploded pictorial view of a device in accordance with the invention.

DETAILED DESCRIPTION OF THE INVENTION

Figure 3:
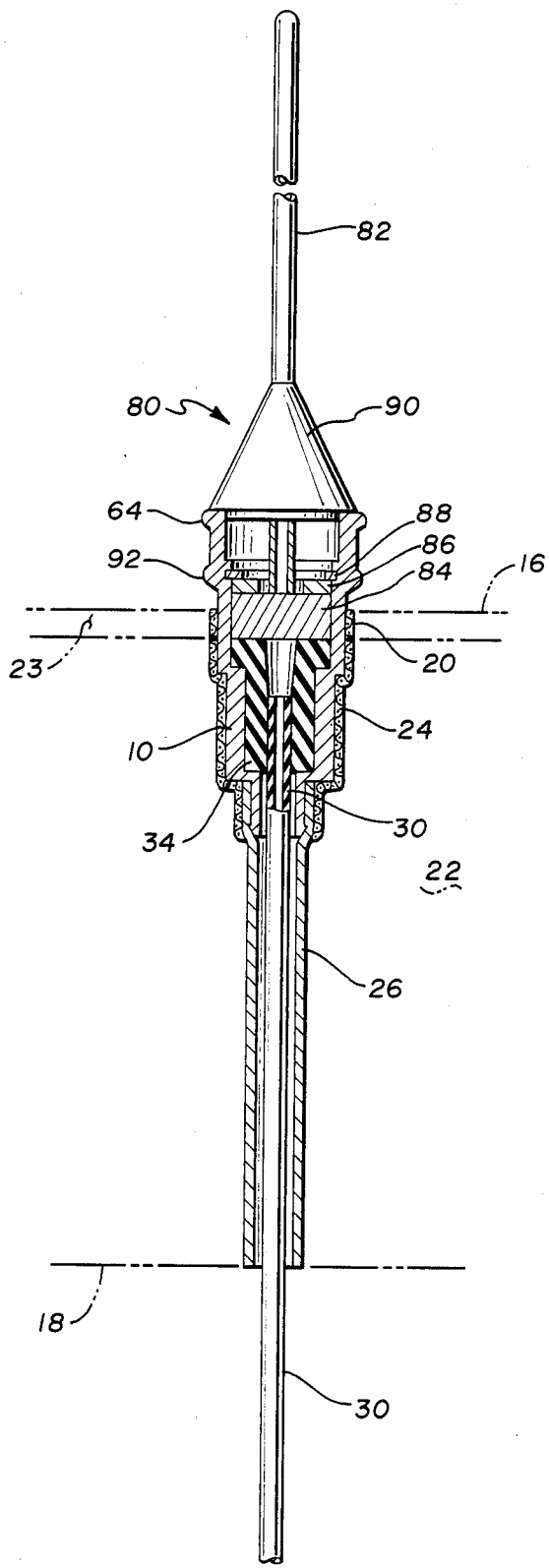
FIG. 3 is a side elevational view of the device and insertion cap with parts cut away.

A preferred embodiment of the invention is shown in FIGS. 1 and 2. A rigid tubular percutaneous body 10 and attached flexible sleeve member 12 including distal end 14 are implanted between the skin layers 16 and the peritoneal wall 18. Rigid tubular body 10 is preferably made of titanium which may be coated with vapor-deposited carbon or other biocompatible coatings. Alternatively, body 10 may remain uncoated. Body 10 is preferably about one inch long (25 mm) with about 0.3 inches (8 mm) of body 10 extending above the skin surface.

Tissue ingrowth media is affixed to the exterior of body 10 as a porous flexible sleeve member or cuff 12. Flexible sleeve member 12 serves as a tissue ingrowth media which stabilizes the implant and prevents its extrusion. Flexible sleeve 12 is preferably made of a material such as the expanded polyethylene terephthalate sold under the trademark Dacron ® by E. I. DuPont de Nemours of Wilmington, Del. and high porosity polytetrafluoroethylene.

It has been found that the outer, nonvascular layer of the skin composed of epithelial tissues has different ingrowth characteristics from the underlying vascular connective tissue of the skin. Surprisingly better ingrowth has been found when flexible sleeve member 12 which contacts the epidermis 23 is formed of an expanded, 90 to 120 pore polytetrafluoroethylene material such as materials sold under the trademark Gor-Tex ® by W. L. Gore Company of Newark, Del. or IMPRAgraph by IMPRA, Inc. of Tempe, Ariz. The polytetrafluoroethylene portion 20 of flexible sleeve member 12 preferably extends from slightly below skin line 16 and extends just inside the dermis shown at 22. The polytetrafluoroethylene (hereinafter referred to as "PTFE") portion 20 of flexible sleeve member 12 is preferably about one to eight millimeters in width. This compares to a typical epidermis depth of about 0.05 inches (13 mm). The PTFE portion 20 extends to where the polyethylene terephthalate portion 24 begins. As an alternative to the use of the polyethylene terephthalate portion 24, a porous titanium coating on body 10 may be used. Such coatings are described for related devices used in blood access applications in commonly owned U.S. Pat. No. 4,405,319 the disclosure of which is incorporated herein by reference.

Catheter guide or conduit 26 extends distally from the distal end of tubular body 10. Catheter conduit 26 is preferably formed of a low porosity PTFE as described above such as has been commonly used in prior art for indwelling blood access prothesis used in hemodialysis. Preferably, catheter conduit 26 is about a five inch long tube which is slipped over the distal end of tubular body 10 where it is held in place by mechanical means in addition to a friction fit on ridge 28.

Catheter conduit 26 provides an open passageway through which catheter 30 is inserted. Catheter conduit 26 provides a guide for catheter 30 and facilitates removal of catheter 30 from the implant by preventing internal tissue ingrowth to the catheter. Conduct 26 is normally trimmed to end at the peritoneal wall 18, to which it is preferably sewn thereto.

Catheter 30 is preferably formed from an approximately 16 to 18 centimeter long tube of a medical grade silicon elastomer. Catheter 30 may be guided into a desired position with the aid of a stiffening rod or wire (not shown).

Proximal end portion 32 of catheter 30 is joined to a catheter plug member 34 which is preferably made of a silicone elastomer. Plug member 34 may alternatively be manufactured as part of the original catheter. Plug member 34 is configured so as to sealably conform to the interior bottom and sides of tubular body 10. A silicone elastomer flange member 36 defines an opening 38 in the plug member which provides connection to the interior of catheter 30. The upper surface of flange member 36 provides a seat for a closure septum 40 which provides an interruptable seal means between the exterior of the body and the body interior. Septum 40 is held in place by a rigid pressure plate 42, which defines an opening 43 therethrough, and by retaining ring 44. Pressure plate 42 is preferably of a molded ABS polymer or titanium. Details of preferred septum constructions and alternates of septum retaining means are disclosed in co-pending application assigned to the same assignee as the present invention, Ser. No. 314,569, filed Oct. 26, 1981 and and U.S. Pat. Nos. 4,417,888 and 4,405,320 the disclosures of which are incorporated herein by reference.

Preferred septum closure 40 includes a preformed needle opening 46 slit through the septum and extending from near the center of the septum out to the edge thereof. The edges of septum 40 have a groove 50 therein encircling the entire body thereof. Groove 50 carries an elastomeric ring 52 which preferably has an eliptical or circular cross section. Ring 52 is in compression around septum 40 and serves to hold the slit septum together and maintain the slit surfaces together in sealed relationship by applying an inwardly directed radial force on septum 40.

The septum is also preferably provided with an elongated bottom recess 54 and a generally semi-spherical top recess 56 which is aligned with hole 43 in pressure plate 42 when assembled within body 10. Bottom recess 54 allows for expansion of the septum when a cannula is inserted therethrough. Top recess 56 provides a cannula receiving guide.

A sponge 58 is inserted into recess 60 which is formed above rigid pressure plate 42 within body 10 of the implant. Sponge 58 is preferably saturated with an antiseptic solution such as Betadine ® (polyvinylpyrolidone/iodine solution) sold by Purdue Frederick Co. of Norwalk, Conn. for maint cavity of body 10.

A penetrable cap member 62 of a flexible, resealable plastic is placed over the end of body 10 which extends above the skin line 16. Body 10 preferably includes a raised lip 64. Penetrable cap member 62 is preferably constructed and arranged as shown in FIGS. 1 and 2 such that a snap fit is accomplished between cap member 62 and lip 64 of body 10. Preferably, a seal is insured by the use of an elastomeric O-ring 66 held within an annular recess within penetrable cap member 62 as shown. Elastomeric ring 66 may be formed integrally with cap member 62.

The implant is accessed through the use of a cannula or needle 70 which is preferably formed of type 305 stainless steel with a circular bore of approximately 0.010 to 0.015 inches (0.214 0.4 mm) in diameter. Cannula 70 may be attached to a conventional syringe or to any pumping systems such that a predetermined volume of insulin or other material may be injected through the implant.

As an aid to inserting cannula 70 into the implant, penetrable cap member 62 preferably includes a cone-shaped depression 72 on its exterior surface and a slit 73 cut therethrough. Depression 70 forms a guide which may be readily felt by visually impaired patients. Penetrable cap member 62 also preferably is provided with an elongated bottom recess 74 which allows for some displacement of cap member 62 when cannula 70 is inserted therethrough.

In operation, body 10 is permanently implanted and catheter conduit 26 is inserted into body 10 by a physician into the patient. PTFE portion 20 becomes securely embedded in the epidermis and the remainder of the flexible sleeve member 12 provides further tissue ingrowth to stabilize the implant. Catheter 30 is guided through body 10 and conduit 26. A stiffening rod may be used to accurately position the distal end of catheter 30.

As an aid in inserting body 10 and conduit 26 within the skin, an insertion cap 80 may be utilized. Insertion cap 80 includes a plastic tube 82 formed with an enlarged end 84, which may be formed of polyvinyl chloride. A pressure plate 86 is fitted over tube 82 and a retaining ring 88 is positioned over pressure plate 86. A cone-shaped cap 90 is then slid over tube 82 above retaining ring 88 as shown in FIG. 3.

A second ridge 92 between the skin line and lip 64 is preferably provided on device 10 so that the device may be held by means of a forceps during implantation and component replacements. A suitable forceps tool for gripping ridge 92 is described in commonly owned co-pending application, Ser. No. 209,058, filed Nov. 21, 1980, the disclosure of which is incorporated herein by reference.

Insertion cap 80 is assembled and inserted into the interior of body 10 prior to implantation. A septum assembly insertion tool as described in co-pending application Ser. No. 209,058 filed Nov. 21, 1980, is preferably used to load insertion cap 80 within the body 10. A physician may then thread tube 82 out through a stab incision in the skin. A pull on tube 82 causes the device to move into the incision as desired. The streamlined configuration of insertion cap 80 decreases the friction encountered in positioning the device. Less preferably, suture thread may be utilized instead of tube 82 such that the physician pulls the device into position with the string.

Septum 40, pressure plate 42 and retaining ring 44 are then positioned within body 10, preferably as a unit with the aid of the septum assembly insertion tool referenced above.

Sponge 58 is inserted into recess 60 and may be saturated with antiseptic at this time.

The unique design of the insulin dispenser implant of the invention prevents extrusion of the device by tissue rejection due to its unique flexible sleeve member. The combined action of the polytetrafluoroethylene portion and the polyethylene terephthalate portion provides good embedment. The entire implant is stabilized within the skin and infection within the peritoneal cavity is minimized due to the presence of a bacterial barrier presented by the antiseptic saturated sponge. Bacteria which enter the interior of tubular body 10 cannot reach the peritoneal cavity due to the antiseptic which saturates the sponge.

Since catheter tubes are prone to cloggage when implanted within the body, it is desirable to provide a means for readily replacing clogged catheters. The catheter of the implant of the invention may be easily replaced without disturbing the tissue ingrowth surrounding the body of the insulin dispenser. The assembly process is merely reversed to gain access to the catheter. Catheter conduit 26 facilitates removal of the catheter by providing an extension into the peritoneal cavity that may adhere to body tissue rather than the catheter itself. The guide therefore shields the catheter from tissue ingrowth so that the catheter may be easily withdrawn from the peritoneal cavity. Invasive surgery is not required in changing catheter tubing.

In considering this invention, it should be remembered that the present disclosure is illustrative only, and that the scope of the invention should be determined by the appended claims.

What is claimed is:

1. A percutaneous implant device for providing access to the peritoneal cavity comprising:

a substantially rigid, tubular percutaneous body of biologically compatible material which extends through the skin and peritoneum when implanted so as to provide means for accessing the peritoneal cavity through the interior of said device;

flexible, subcutaneous catheter means associated with said tubular percutaneous body for providing fluid communication between the body exterior and the peritoneal cavity;

porous tissue ingrowth means for anchoring the device to a patient's body said porous tissue ingrowth means including a porus collar of polytetrafluoroethylene overlaying said tubular percutaneous body on the portion of said tubular body to be embedded within the epidermis and a porous collar of polyethylene terephthalate overlaying said tubular percutaneous body between said polytetrafluoroethylene collar and said catheter;

an elastomeric septum member occupying a portion of the tubular portion of said body, and means for holding said septum member in a sealed relationship within the interior of said tubular percutaneous body, said septum and said body defining an excutaneous cavity within the device;

sponge means within said excutaneous cavity for maintaining sterility when saturated with an antiseptic solution; and a penetrable cap member adapted to be joined to said body for sealing said sponge means within said tubular percutaneous body of said device.

2. A percutaneous implant device for providing access to the peritoneal cavity comprising:

a substantially rigid, tubular percutaneous body of biologically compatible material which extends through the skin and peritoneum when implanted so as to provide means for accessing the peritoneal cavity through the interior of said device;

flexible, subcutaneous catheter means associated with said tubular percutaneous body for providing fluid communication between the body exterior and the peritoneal cavity;

porous tissue ingrowth means for anchoring the device to a patient's body;

an elastomeric septum member occupying a portion of the tubular portion of said body, and means for holding said septum member in a sealed relationship within the interior of said tubular percutaneous body, said septum and said body defining an excutaneous cavity within the device;

sponge means within said excutaneous cavity for maintaining sterility when saturated with an antiseptic solution;

a penetrable cap member adapted to be joined to said body for sealing said sponge means within said tubular percutaneous body of said device; and an insertion cap means is provided for pulling said device through a skin, said insertion cap means including a generally conical cap and a tube extending through the apex of said conical cap, said tube secured at one end to said tubular percutaneous body by a retaining ring and pressure plate.

* * * * *

UNITED STATES PATENT AND TRADEMARK OFFICE
CERTIFICATE OF CORRECTION

PATENT NO. : 4,781,693
DATED : November 1, 1988
INVENTOR(S) : Martinez et al

It is certified that error appears in the above-identified patent and that said Letters Patent is hereby corrected as shown below:

Col. 1, line 39, delete "implemented" and insert

- implanted -

Signed and Sealed this

Seventh Day of March, 1989

Attest:

DONALD J. QUIGG

Attesting Officer    Commissioner of Patents and Trademarks